US009566027B2

United States Patent
Tamir

(10) Patent No.: US 9,566,027 B2
(45) Date of Patent: Feb. 14, 2017

(54) DEVICE AND SYSTEM FOR BLOOD SAMPLING

(75) Inventor: Nili Tamir, Zihron Yaakov (IL)

(73) Assignee: RAPIDX LTD., Tel Aviv (IL)

( * ) Notice: Subject to any disclaimer, the term of this patent is extended or adjusted under 35 U.S.C. 154(b) by 985 days.

(21) Appl. No.: 13/806,512

(22) PCT Filed: Jun. 23, 2011

(86) PCT No.: PCT/IL2011/000504
§ 371 (c)(1),
(2), (4) Date: Mar. 14, 2013

(87) PCT Pub. No.: WO2011/161681
PCT Pub. Date: Dec. 29, 2011

(65) Prior Publication Data
US 2013/0172711 A1    Jul. 4, 2013

Related U.S. Application Data

(63) Continuation of application No. 12/822,650, filed on Jun. 24, 2010, now abandoned.

(51) Int. Cl.
*G01N 21/75* (2006.01)
*G01N 31/22* (2006.01)
(Continued)

(52) U.S. Cl.
CPC ..... *A61B 5/150114* (2013.01); *A61B 5/14546* (2013.01); *A61B 5/14552* (2013.01);
(Continued)

(58) Field of Classification Search
USPC ....................................................... 422/410
See application file for complete search history.

(56) References Cited

U.S. PATENT DOCUMENTS

| 4,627,445 A | 12/1986 | Garcia et al. |
| 5,518,006 A | 5/1996 | Mawhirt et al. |

(Continued)

FOREIGN PATENT DOCUMENTS

| DE | 4234553 A1 | 4/1993 |
| DE | 29904112 U1 | 5/1999 |

(Continued)

OTHER PUBLICATIONS

Monika Menta, et al., Emerging technologies in diabetes care, U.S. Pharmacist, Nov. 2002, pp. 29-48, vol. 27, No. 11.

*Primary Examiner* — Jill Warden
*Assistant Examiner* — Brittany Fisher
(74) *Attorney, Agent, or Firm* — Browdy and Neimark, PLLC

(57) ABSTRACT

A medical device is presented for reduced-pain blood sampling and testing. The device comprises a housing defining a finger site for supporting a user's finger or a portion thereof within said finger site during the device operation; piercing, sampling and testing assemblies sequentially actuatable to successively initiate piercing, sampling and testing operational modes of the device; a carriage at least partially accommodated within said housing and being adapted for movement with respect to said finger site between its first position corresponding to the piercing mode of the device and a second position corresponding to the sampling and testing modes of the device, the device being thereby capable of operating in the piercing, sampling and testing modes while at a static position of the user's finger.

19 Claims, 11 Drawing Sheets

(51) Int. Cl.
  *A61B 5/15* (2006.01)
  *A61B 5/1455* (2006.01)
  *A61B 5/00* (2006.01)
  *A61B 5/157* (2006.01)
  *A61B 5/151* (2006.01)
  *G01N 33/52* (2006.01)
  *A61B 5/145* (2006.01)

(52) U.S. Cl.
  CPC ........ *A61B 5/157* (2013.01); *A61B 5/150022* (2013.01); *A61B 5/15087* (2013.01); *A61B 5/15105* (2013.01); *A61B 5/15113* (2013.01); *A61B 5/15117* (2013.01); *A61B 5/15142* (2013.01); *A61B 5/15144* (2013.01); *A61B 5/150358* (2013.01); *A61B 5/150412* (2013.01); *A61B 5/150519* (2013.01); *A61B 5/150748* (2013.01); *A61B 5/150824* (2013.01); *A61B 5/6826* (2013.01); *A61B 5/6838* (2013.01); *A61B 5/14532* (2013.01)

(56) References Cited

U.S. PATENT DOCUMENTS

| | | |
|---|---|---|
| 5,662,127 A | 9/1997 | De Vaughn |
| 5,893,870 A | 4/1999 | Talen et al. |
| 6,045,567 A | 4/2000 | Taylor |
| 6,093,156 A | 7/2000 | Cunningham et al. |
| 6,278,889 B1 | 8/2001 | Robinson |
| 6,400,972 B1 | 6/2002 | Fine |
| 6,626,598 B2 | 9/2003 | Schneider |
| 6,679,852 B1 | 1/2004 | Schmelzeisen-Redeker et al. |
| 2002/0052618 A1 | 5/2002 | Haar |
| 2003/0060730 A1 | 3/2003 | Perez |
| 2003/0191415 A1 | 10/2003 | Moerman et al. |
| 2004/0249252 A1* | 12/2004 | Fine ............ A61B 5/0059 600/322 |
| 2005/0033133 A1 | 2/2005 | Kraft |
| 2005/0038463 A1 | 2/2005 | Davar |
| 2005/0234486 A1 | 10/2005 | Allen |
| 2005/0240119 A1 | 10/2005 | Draudt et al. |
| 2006/0094985 A1 | 5/2006 | Aceti et al. |
| 2006/0173380 A1* | 8/2006 | Hoenes ............ A61B 5/1411 600/583 |
| 2006/0195133 A1* | 8/2006 | Freeman ............ A61B 5/1411 606/181 |
| 2006/0224085 A1 | 10/2006 | Nakayama et al. |
| 2007/0043281 A1 | 2/2007 | Fine |
| 2007/0078360 A1 | 4/2007 | Matsumoto et al. |
| 2007/0088377 A1 | 4/2007 | LeVaughn et al. |
| 2008/0033319 A1 | 2/2008 | Kloepfer et al. |
| 2008/0077048 A1* | 3/2008 | Escutia ............ A61B 5/1411 600/583 |
| 2008/0262324 A1 | 10/2008 | Van Der Voort et al. |
| 2008/0262387 A1* | 10/2008 | List ............ A61B 5/1411 600/583 |
| 2009/0177224 A1 | 7/2009 | Naghavi et al. |

FOREIGN PATENT DOCUMENTS

| | | |
|---|---|---|
| DE | 10315396 A1 | 10/2004 |
| EP | 1157660 A1 | 11/2001 |
| EP | 1374770 A1 | 1/2004 |
| EP | 1586268 A2 | 10/2005 |
| EP | 2184012 A1 | 5/2010 |
| JP | 9266889 A | 10/1997 |
| WO | 2004064637 A2 | 8/2004 |
| WO | 2007042137 A2 | 4/2007 |
| WO | 2008027319 A2 | 3/2008 |
| WO | 2008155756 A2 | 12/2008 |
| WO | 2009081405 A2 | 7/2009 |

\* cited by examiner

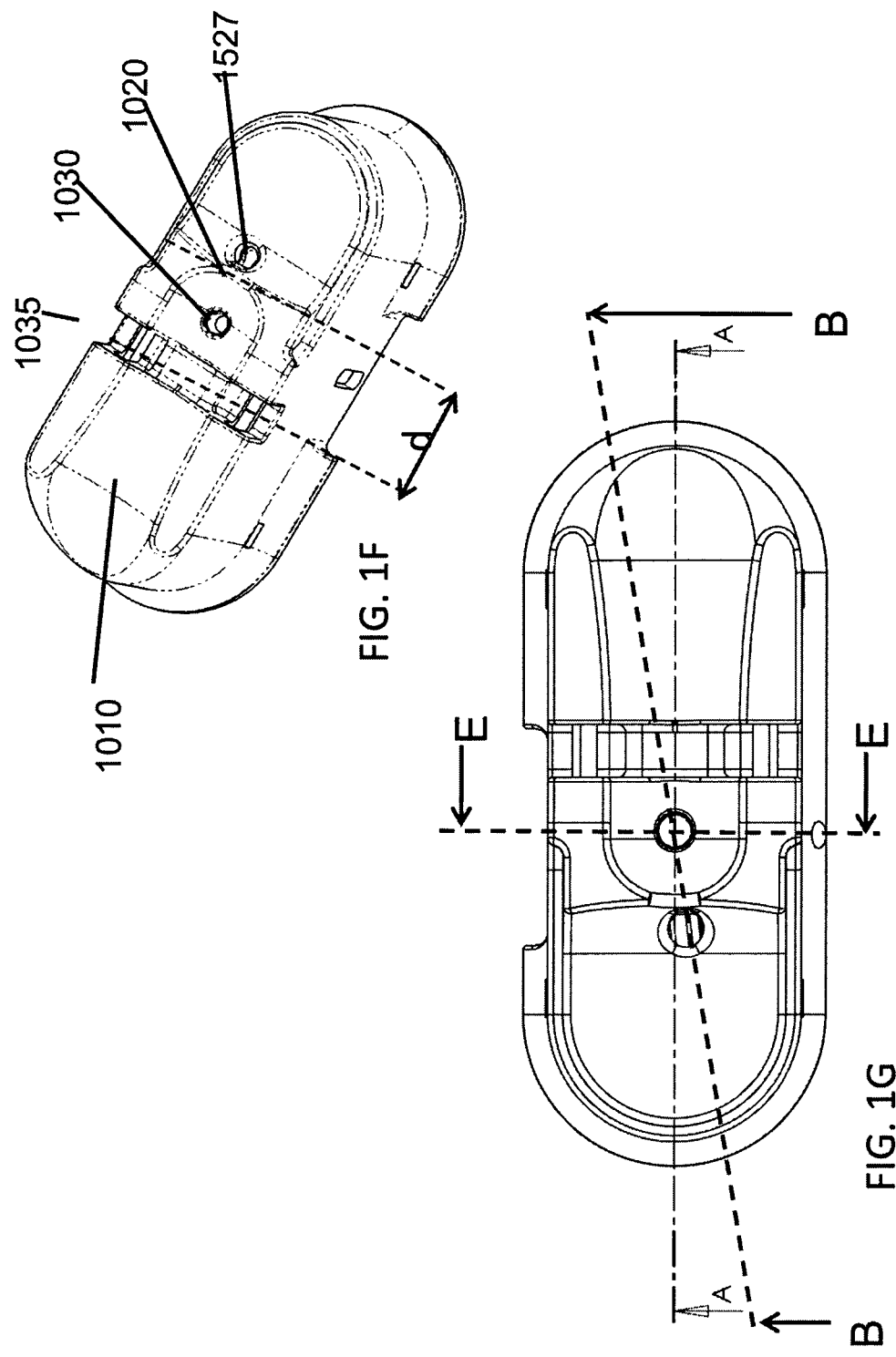

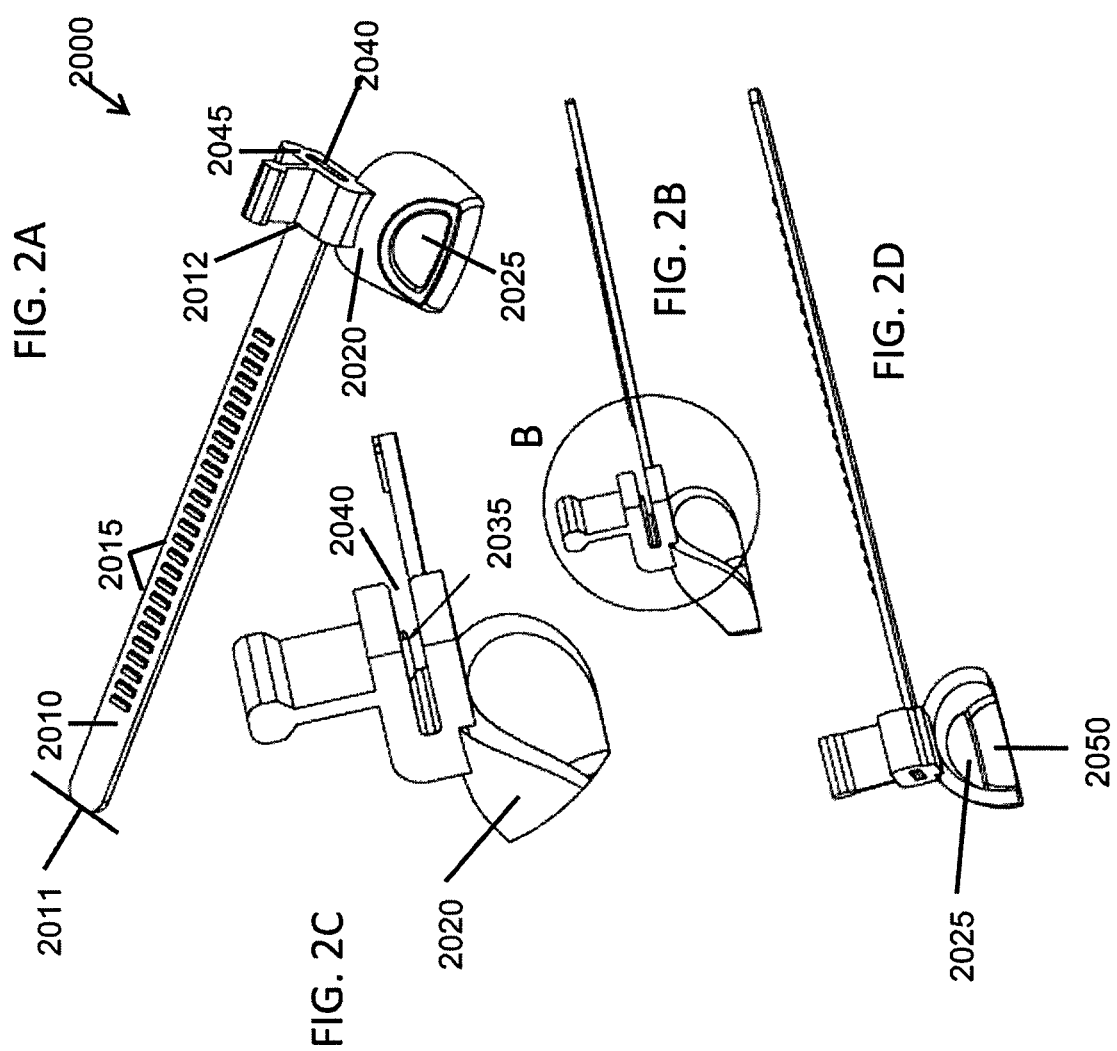

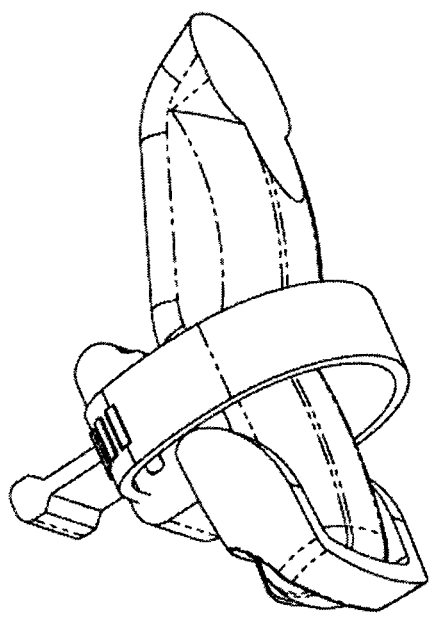 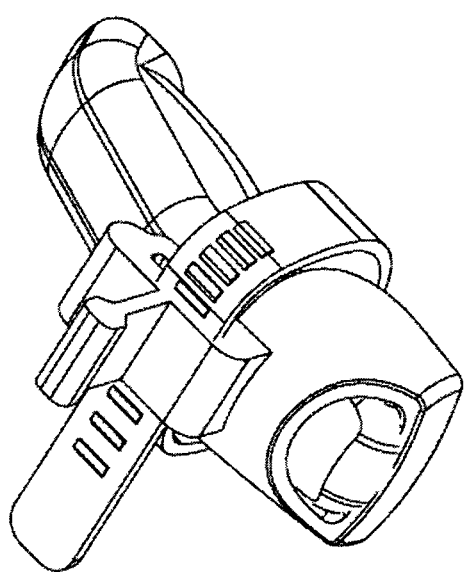
FIG. 2I
FIG. 2J

DEVICE AND SYSTEM FOR BLOOD SAMPLING

FIELD OF THE INVENTION

The present invention relates generally to blood sampling techniques, and more specifically to a device for reduced-pain blood sampling.

BACKGROUND OF THE INVENTION

There are many instances in which a person must undergo body fluid sampling. Medical practitioners often require full blood analyses to assist in the diagnosis of a disease or condition. Diabetics, for example, must monitor their blood sugar a number of times a day. The removal or blood from a human body is normally performed invasively and tends to be painful, leading to procrastination and non-compliance of the patients. Moreover, in children and babies, the invasive procedures are more difficult and less effective. There is therefore a need to develop both less painful invasive procedures and non-invasive procedures for blood and other body fluid removal.

Some devices and methods for invasive blood sampling are described in the art, inter alia, U.S. Pat. No. 6,045,567 describes a lancing device, having a spring-loaded lancet holder slidably mounted within a housing for carrying a disposable lancet and needle. A knob on the back of the device has forward-extending fingers that stop the lancet holder at an adjustable predetermined point after the device has been fired. The fingers not only control the penetration depth of the needle, but also absorb vibrations and reduce noise to cause less pain to the user.

US 2005/038463 describes a device for providing transcutaneous electrical stimulation (TENS) to the finger of a patient at the same time that the finger is being punctured for the purpose of obtaining a blood sample. The device should reduce the pain associated with this procedure and should be of particular interest to diabetic patients that must perform repeated finger puncture procedures to monitor blood glucose levels.

US 2005/234486 describes an apparatus for extracting bodily fluid (e.g., whole blood) from a user's finger includes a housing with a lancing mechanism and a clamping mechanism attached to thereto. The clamping mechanism includes a lower arm assembly and an upper arm assembly. The upper and lower arm assemblies are operatively connected such that when a user's finger applies a user force to the lower arm assembly and displaces the lower arm assembly from a first to a second position, the upper and lower arm assemblies cooperate to engage the user's finger with a compressive force that is greater than the user force. In addition, the lancing mechanism is configured to lance a target site on the user's finger while the upper and lower arm assemblies are cooperating to engage the user's finger. Thereafter, the compressive force serves to extract a bodily fluid sample from the lanced target site.

US 2006/224085 describes a method for collecting small amounts of blood sample by painless puncture of a finger. When puncture of skin of a human being by a needle or another device is performed at the depth of no more than 0.5 mm, pain accompanied by the puncture is diminished or decreased. Regardless of an error in the depth of the puncture, the depth of puncture always needs to not exceed this depth. The site of puncture is the dorsal surface of a finger, that is, the area from finger joint (IP joint of thumb, DIP joint of fingers other than thumb) to proximal nail wall and the area extending from proximal nail wall to lateral nail wall.

Some devices and methods for non-invasive blood sampling are described in the art, inter alia, U.S. Pat. No. 6,400,972 describes an over-systolic pressure, which is applied to a patient's blood perfused fleshy medium. The pressure causes a state of temporary blood flow cessation within a time period insufficient for irreversible changes in the fleshy medium. Release of the over systolic pressure causes a state of transitional blood flow terminating with the normal blood flow. At least two sessions of measurement, separated in time, are executed and at least one of these sessions is selected within the time period including the state of temporary blood flow cessation and the state of transitional blood flow. Optical non-invasive measurement of the concentration of at least one blood constituent are successively performed at these at least two sessions, and respective values of the concentration are obtained.

US 2004/249252 describes a method and device for use in non-invasive optical measurements of at least one desired characteristic of patient's blood. A condition of artificial blood kinetics is created at a measurement location in a patient's blood perfused fleshy medium and maintained for a certain time period. This condition is altered over a predetermined time interval within said certain time period so as to modulate scattering properties of blood. Optical measurements are applied to the measurement location by illuminating it with incident light beams of at least two different wavelengths in a range where the scattering properties of blood are sensitive to light radiation, detecting light responses of the medium, and generating measured data indicative of time evolutions of the light responses of the medium for said at least two different wavelengths, respectively, over at least a part of said predetermined time interval.

US 2007/043281 describes a method and system for non-invasive measurements in a patient's body in which several measurement sessions are performed on a measurement location. Each measurement session includes applying an external electromagnetic field to the measurement locations, detecting at least two responses of the measurement location, and generating data indicative of the detected response. These responses are characterized by at least two different values of a controllable parameter. The measurement sessions include at least two measurement sessions carried out at a normal blood flow in the measurement location and at least two measurement sessions carried out at a condition of artificial kinetics in the measurement location. The first and second measured data are processed to determine a first relation between the first time variations and a second relation between the second time variations for the different parameter that can be used to determine the at least one blood related parameter.

US 2008/262324 describes an efficient approach of attaching and fixing a measurement head for a spectroscopic system to a variety of different parts of the skin of a patient. The measurement head preferably features a compact design providing a flexible handling and offering a huge variety of application areas taking into account the plurality of properties of various portions of the skin. Furthermore, the measurement head features a robust and uncomplicated optical design not requiring a lateral shifting of the optical axis of the objective. Such transverse relative movements between the objective and a capillary vessel in the skin are preferably performed by mechanically shifting the skin with respect to the objective of the measurement head. Moreover, the measurement head is adapted to host one or more pressure sensors measuring the contact pressure between the measurement head and the skin. This pressure information can further be exploited in order to calibrate the spectroscopic analysis means, to regulate the contact pressure within predefined margins specifying an optimum range of contact pressure for spectroscopic examination of capillary vessels.

Most of the non-invasive devices in the art require occasional calibration involving invasive blood sampling. There is therefore a need to provide systems, devices and methods for blood sampling which overcome the limitations and disadvantages of the devices and methods described hereinabove.

GENERAL DESCRIPTION

There is a need in the art in a medical device for a blood test, which is on the one hand portable and easy to operate (e.g. by user himself) to perform a full and accurate blood sampling and preferably also perform a test of a desired condition of blood, and on the other hand is configured to reduce pain associated with the blood sampling procedures.

The present invention meets the above goals by providing a novel device for the blood test, as well as a finger holding element which may be a stand-alone unit.

With regard to the pain reduction aspect of the invention, it should be understood that "pain" has both psychological and physical factors. The device of the present invention is configured such that it on the one hand hides an operation of a finger piercing assembly from the user (thus reducing the psychological factor), and on the other hand allows for appropriately applying pressure to the finger (i.e. pressure value control and positioning of a pressurized location) to thereby reduce the physical effect of pain.

The device of the present invention may be fully integrated with respect to all the necessarily elements for performing the test: piercing assembly (including e.g. a needle or a small scalpel), sampling assembly and testing assembly. The device allows for performing the test within the device and/or collecting the blood sample for further test by an external device.

Moreover, the device of the present invention provides for a passive extraction of a blood sample from the finger, namely the finger may be kept static during the entire test procedure, while all the elements for piercing, sampling and testing modes are orderly brought into operation (e.g. brought to the desired location with respect to the finger and actuated). The device is preferably configured to be in a stable state eliminating a need for holding the device by the second hand of the same user or another assistant. Furthermore, the device of the present invention provides for controlling the collection of the desired volume of blood for the test, i.e. sufficient amount of blood on the one hand and not exceeding the predetermined volume to suit the testing reagents being used.

Thus, according to one broad aspect of the invention, there is provided a medical device for a blood test, the device comprising:

i. a housing defining a finger site for supporting a user's finger or a portion thereof within said finger site during the device operation;

ii. piercing, sampling and testing assemblies configured to be sequentially actuatable to successively initiate piercing, sampling and testing operational modes of the device;

iii. a carriage at least partially accommodated within said housing and being adapted for movement with respect to said finger site between its first position corresponding to the piercing mode of the device and a second position corresponding to the sampling and testing modes of the device, the device being thereby capable of operating in the piercing, sampling and testing modes while at a static position of the user's finger supported by the finger site.

The piercing assembly may be accommodated inside the housing being located with respect to the finger site such that an operation of the piercing assembly in the piercing mode of the device is hidden from the user. The sampling assembly comprises a blood holding element (reservoir) for blood collection and is configured for collection of the minimal desired volume of blood sufficient for the test. The testing assembly is constituted at least by a slot made in the housing for selectively using a test strip in said slot and/or a displaceable bottom plate of the sampling assembly (as will be described below), thus either enabling to transfer the reservoir with the collected blood sample to an external test device and/or allowing the collected blood sample to flow from the reservoir onto the test strip located in the device.

The finger holding element is preferably provided, which as indicated above may be stand-alone unit separate from said housing. The finger holding element is configured to be fit on the finger such as to apply pressure to the finger in a manner assisting in withdrawal of blood during the piercing and sampling modes and reducing pain associated with the blood test.

In some embodiments, the finger holder comprises a band operable to be shifted from its open inoperative position to a closed-loop operative position in which it fits the finger. The band, when in the operative position thereof, applies pressure to the finger while preventing over-pressing of the finger, thereby reducing pain involved in the blood test procedures.

In some other embodiments, the finger holder element is configured to be fit on the finger such as to apply pressure to a certain location on the finger, wherein this certain location is selected to be spaced a predetermined distance from the finger tip and/or a piercing orifice provided in the finger site. This can be implemented by providing a groove in the housing located within the finger site and being configured for immobilizingly receiving a portion of the finger holder element therein. By this, a position of the finger with respect to said finger site is fixed during the device operation. The groove is also located at a predetermined distance from the piercing orifice, thereby ensuring the application of pressure to the finger by said finger holder element a certain predetermined distance from a location on the finger being pierced.

Optionally, said housing includes a protrusion defining a distal end of the finger site to be abutted by a finger tip during the device operation. In this case, a finger holding element is configured to be fit on the finger to apply pressure to a location on the finger corresponding to a location spaced a predetermined distance from the protrusion, which is located a predetermined distance from a piercing orifice provided in said finger site.

Preferably, the piercing assembly comprises a piercing element movable along a first axis (typically vertical axis) towards and away from the finger site, and accessing the finger via an orifice in said finger site to perform piercing. The piercing assembly may be stationary mounted in the housing or may be movable by said carriage along a second axis (typically horizontal axis) intersecting with the first axis, with respect to the finger site, between its first inoperative position and second operative position. In the first inoperative position, the piercing element is not aligned with the orifice along the first axis, and in the second operative position it is aligned with said orifice along the first axis.

As indicated above, the sampling assembly comprises a blood holding element defining a cavity having a predetermined volume in accordance with a desired volume of blood to be collected. The configuration of the device is such that a liquid-phase blood sample flows from the finger as a result of piercing into the blood holding element.

Preferably, the sampling assembly is configured such as to enable indication of a condition that the desired blood volume has been collected, and accordingly a user may remove his finger from the finger site. To this end, the sampling assembly is configured to collect excess of extracted blood immediately upon arriving to a condition that the blood holding element is full of blood, and provide a corresponding indication to the user. This can be implemented in several ways, e.g. by using a collecting assembly configured and operable by the principles of capillary method, i.e. once the residual blood enters the capillary, the latter pulls the blood directly to an indication spot; or by allowing the excess/residual blood to freely flow towards an indication window.

For example the blood holding element may be configured such that it is formed, at least when in the sampling mode of the device, with a top portion having a projecting sloped member for flowing a portion of collected blood volume above said predetermined volume out of a hollow liquid reservoir towards an indication window, appearance of blood in the indication window being indicative of that the blood holding element contains the predetermined volume of blood. This means that the top portion may be part of the liquid reservoir, or the blood holding element is a two-part element, the first, bottom part being said liquid reservoir, and the second top part being removably mountable onto the reservoir thereabove. Thus, generally, if provision of the projecting sloped member is considered, it may be associated with the removable top part of the two-part blood holding element or with the top portion of the single-part blood holding element (reservoir).

Considering the two-part form of the blood holding element, the second top part thereof may be movable between its inoperative position being separated (dissembled) from the reservoir and its operative, assembled position forming the top portion of the blood holding element. Displacement of the top portion from the assembled position into the dissembled position might also serve for removing excess blood from the reservoir.

Alternatively or additionally, a separate collecting element (capillary) is used for collecting blood while arriving to the top portion of the blood holding element during the sampling. Appearance of blood in the capillary, when viewed by user, might by itself be indicative of the end of the sampling procedure. Thus, the transparent blood collecting element may present an indication window. Alternatively or additionally, the capillary may also be provided with any suitable sensing and indicating assembly, e.g. an optical sensor and indicator, or an optical sensor and acoustic indicator, etc.

In some embodiments, the liquid reservoir comprises a bottom plate movable between its first and second positions. In the first position, the bottom plate is aligned with side walls of a generally cylindrically shaped reservoir, corresponding to a closed state of the reservoir keeping collected blood in the reservoir. In the second position, the bottom plate is misaligned with the side walls corresponding to an open state of the reservoir allowing blood flow from the reservoir onto a test strip of the testing assembly. Thus, in this configuration, the movable bottom plate of the blood holding element and the test strip form together the testing assembly. As indicated above, the test strip may be insertable into a slot made in the housing. For example, insertion of the test strip into the slot enables sliding movement of the test strip towards and away from a location of alignment with the piercing orifice, i.e. corresponding to the testing mode.

The configuration may generally be such that the test strip is selectively insertable into a position in which a portion thereof is aligned with said liquid reservoir (which might correspond to alignment with a piercing orifice) to receive a blood sample from the finger after piercing.

A test strip may be of any known suitable type. The test strip may for example include a capillary sponge located inside the test strip housing. The latter may include a window for indicating the results of the test. Such a test results window may include a control indicator and a test indicator. The test indicator may include any number of lines, such as between one and three. The results may be quantitative, qualitative, or semi-qualitative.

In some embodiments, reagent transferring assembly are provided for transferring a predetermined amount of at least one reagent to the test strip after blood has been drawn from the finger. The reagent transferring assembly may include at least one container for holding a reagent therein. A syringe-like piston may be provided for pushing the reagent out of an orifice located at the end of the reagent container. It will be appreciated that other reagent transferring means could also be employed for directly conveying at least one reagent to the test strip. It will also be appreciated that in some tests, a reagent is not required whereas in other tests, one or more reagent may need to be added in order for the test to be properly performed.

In some embodiments of the invention, the movable carriage incorporates or is connected to elements of the piercing, sampling and testing assemblies such that the movement of the carriage with respect to the finger site successively brings said elements into different operative positions corresponding to said first and second positions of the carriage. In each of such operative positions, the element of the respective assembly is aligned with the finger site.

The device may also comprise a reagent holding unit mounted for movement such as to be selectively brought into alignment position with respect to an element of the testing assembly (e.g. test strip), when in the testing mode of the device.

According to another broad aspect of the invention, there is provided a medical device for a blood test, the device comprising: a housing defining a finger site for supporting a user's finger or a portion thereof within said finger site during the device operation, and piercing, sampling and testing assemblies at least partially accommodated in said housing, wherein the piercing assembly comprises a piercing element movable towards and away from the finger site accessing the finger via an orifice in said finger site to perform piercing;

the sampling assembly comprises a blood holding element, which comprises a hollow liquid reservoir for collecting blood freely flowing from the orifice, said liquid reservoir comprising a bottom plate movable between its first position, in which it is aligned with side walls of the reservoir, corresponding to a closed state of the reservoir keeping collected blood in the reservoir, and a second position, in which it is misaligned with the side walls corresponding to an open state of the reservoir allowing blood flow from the reservoir onto a test strip of the testing assembly.

According to yet further broad aspect of the invention, there is provided a device for use in a blood test, the device comprising a finger holding element configured to be fit on the finger such as to apply certain pressure to the finger, said finger holder comprising a band operable to be shifted from its open inoperative position to a closed-loop operative position in which it fits the finger, said band when in the operative position thereof applies the pressure to the finger while preventing over-pressing of the finger, thereby reducing pain associated with the blood test.

Such device may comprise a cap-like element configured to accommodate at least a portion of the finger and defining distal and proximal ends, where the distal end has a contact surface, and the proximal end is connected to a portion of said band.

The invention, in its yet further aspect, provides a system comprising the above-described blood test device and a measurement device for non-invasively measuring one or more body parameters.

The measurement device may be configured and operable for non-invasive measurement of blood glucose. This may be performed using at least one of the following measurements: an optical measurement, an impedance-type measurement, a photo-acoustic measurement and an ultrasound tagging-based measurement.

The measurement device may comprise a ring-shaped sensor, which may for example be placeable on the finger in addition to a finger holding element for use in the blood test. The measurement device may comprise a finger encompassing element for applying pressure to the finger.

The test may be selected from the following: a test for biological factors associated with cholesterol; a test for assessing heart disease risk; a glucose test for monitoring diabetes; a test for the presence of illegal drugs; a test for drug abuse; a test for hCG pregnancy testing; a test for an HIV-antibody for determining HIV infection or other infectious diseases, a prothrombin time test for monitoring blood thinning and clotting; a test for fecal occult blood for screening for colorectal cancer or other cancer related tests; a test for luteinizing hormone for determining ovulation, or a combination thereof.

The housing of the device may be formed with a lateral opening appropriately positioned for receiving at least a portion of the test strip. In some embodiments, the test strip has an opening therein for allowing the piercing means to pass therethrough at the time of blood sampling. In these embodiments, blood drawn from the finger tip using the piercing assembly automatically drips back down onto the test strip.

BRIEF DESCRIPTION OF THE DRAWINGS

The invention will now be described in connection with certain exemplary embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1A:
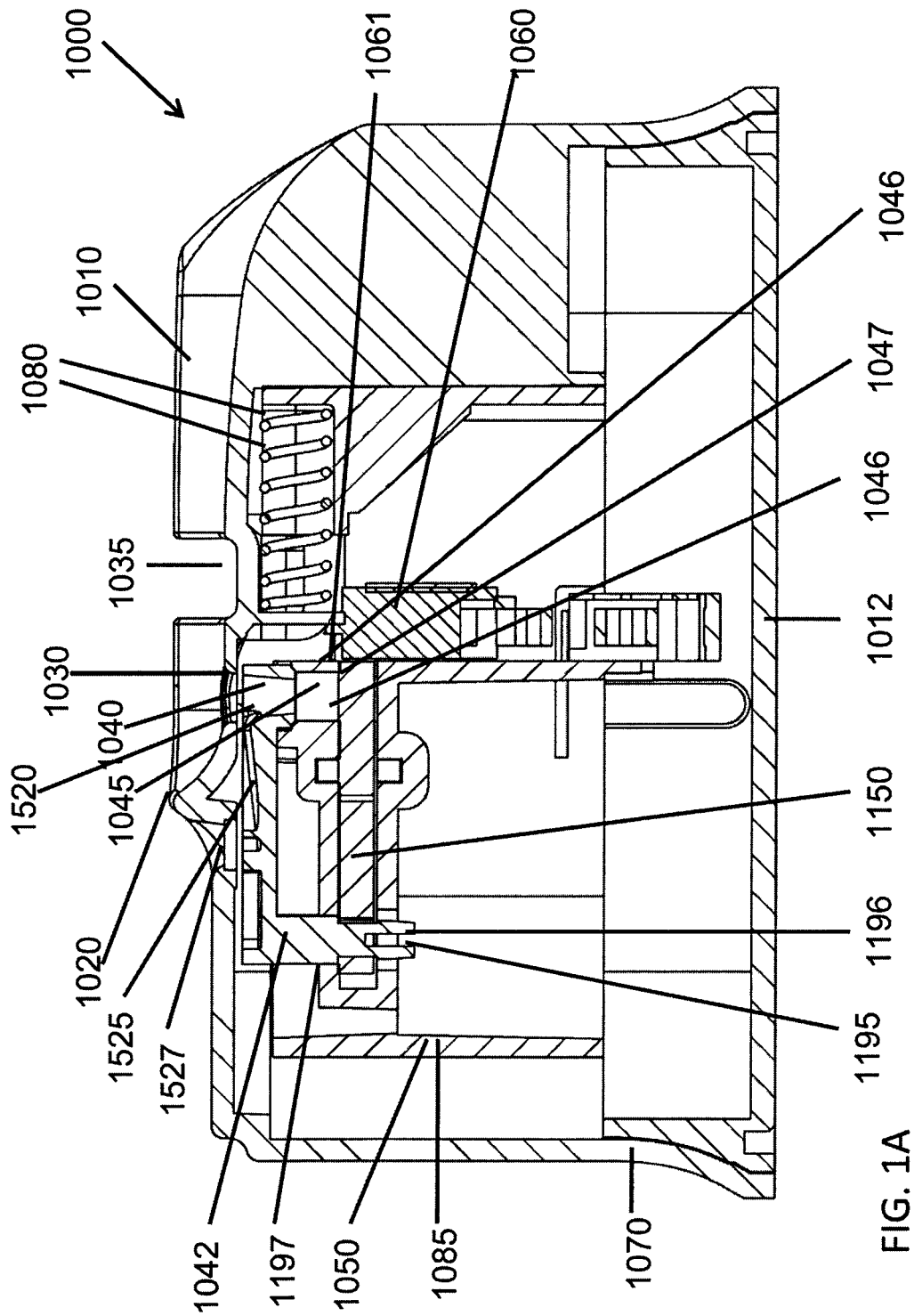
Figure 1B:
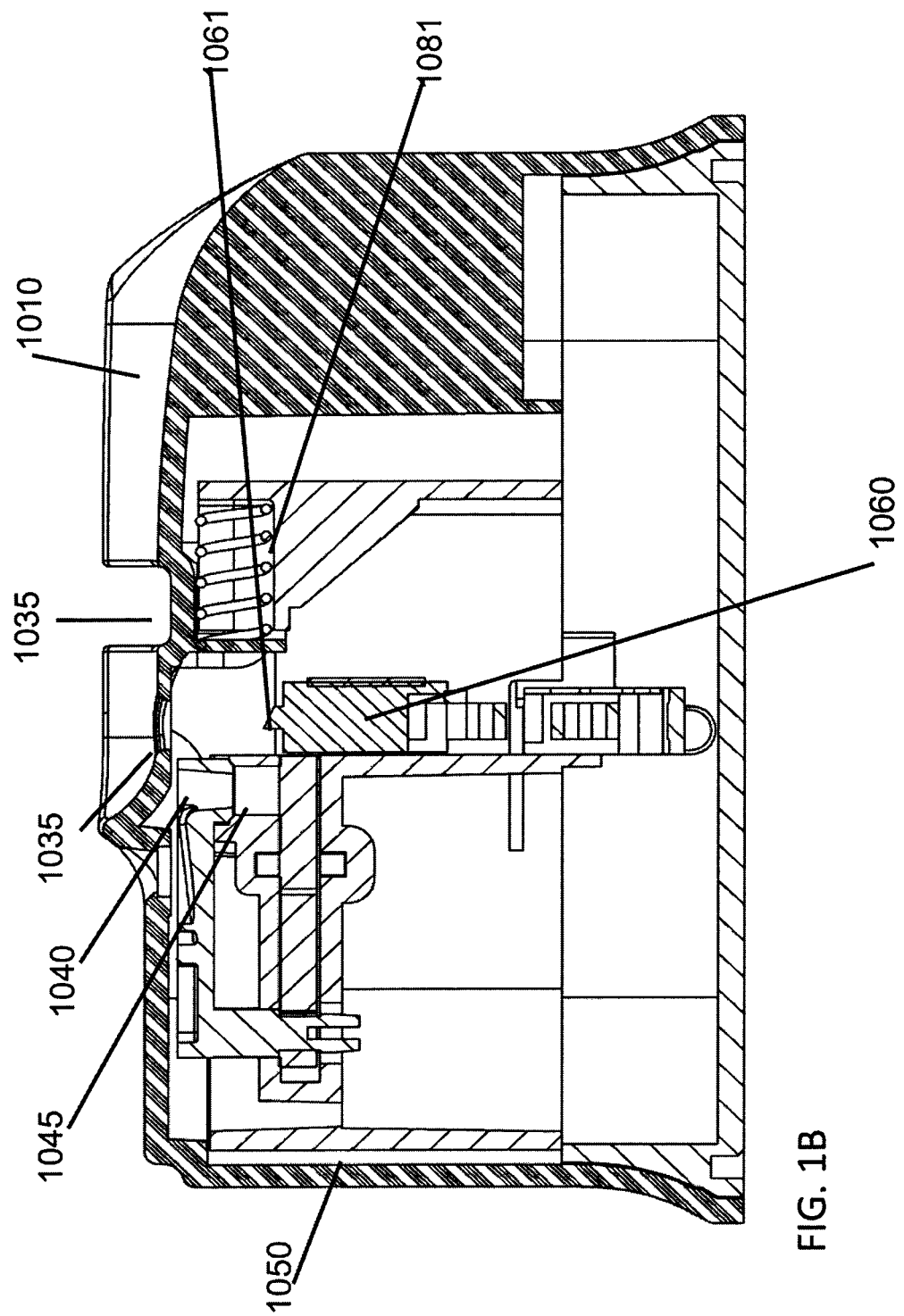
Figure 1C:
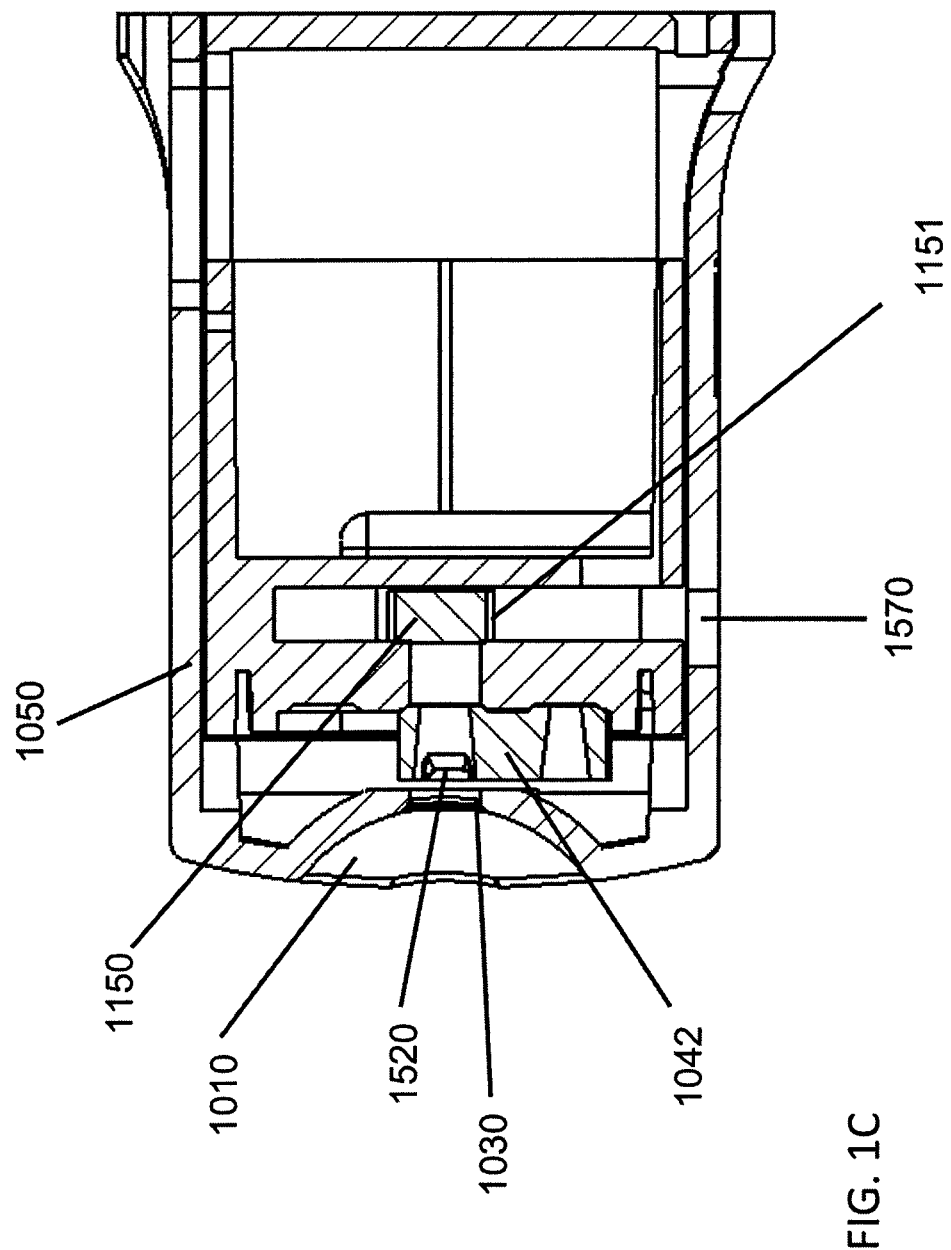
Figure 1D:
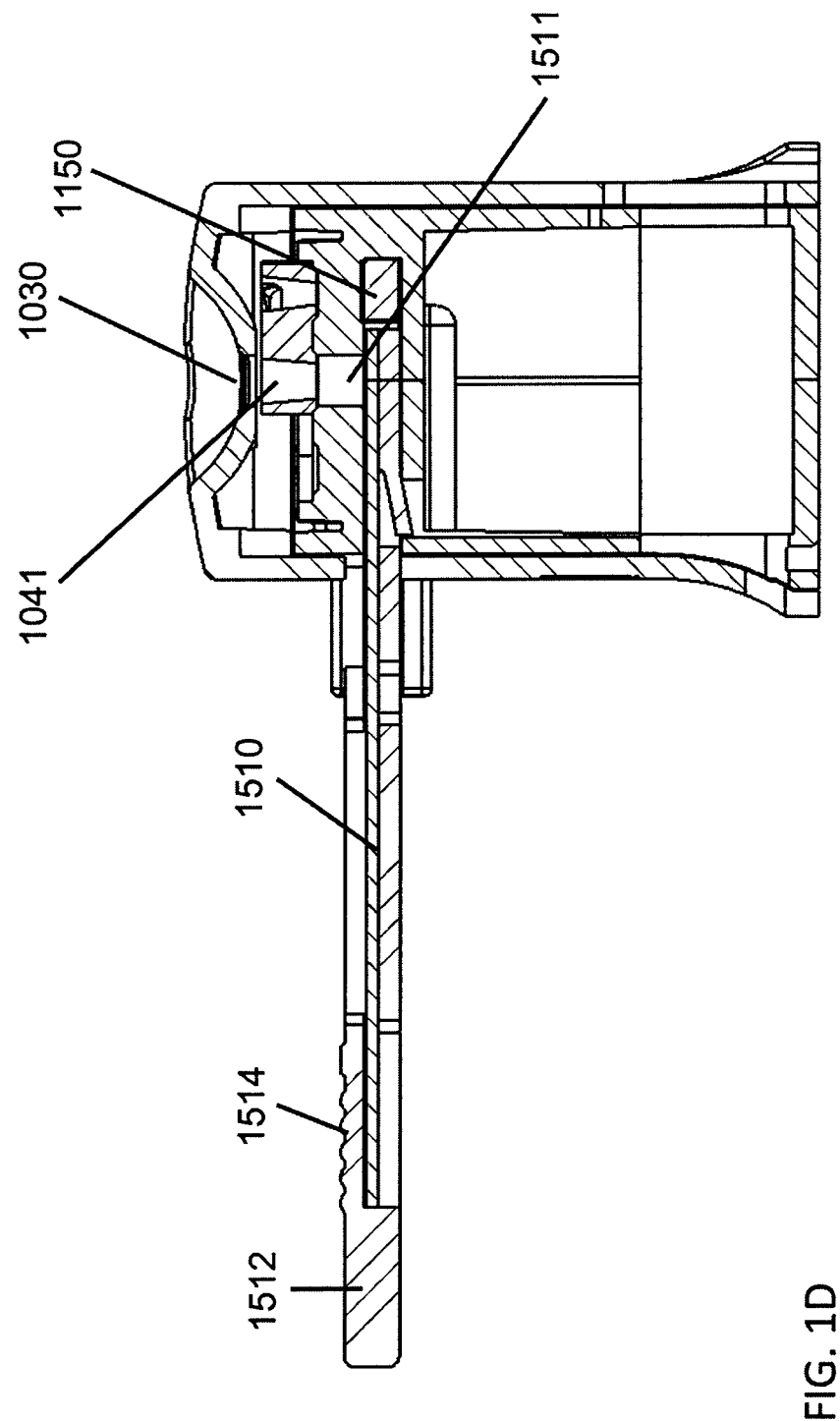
Figure 1E:
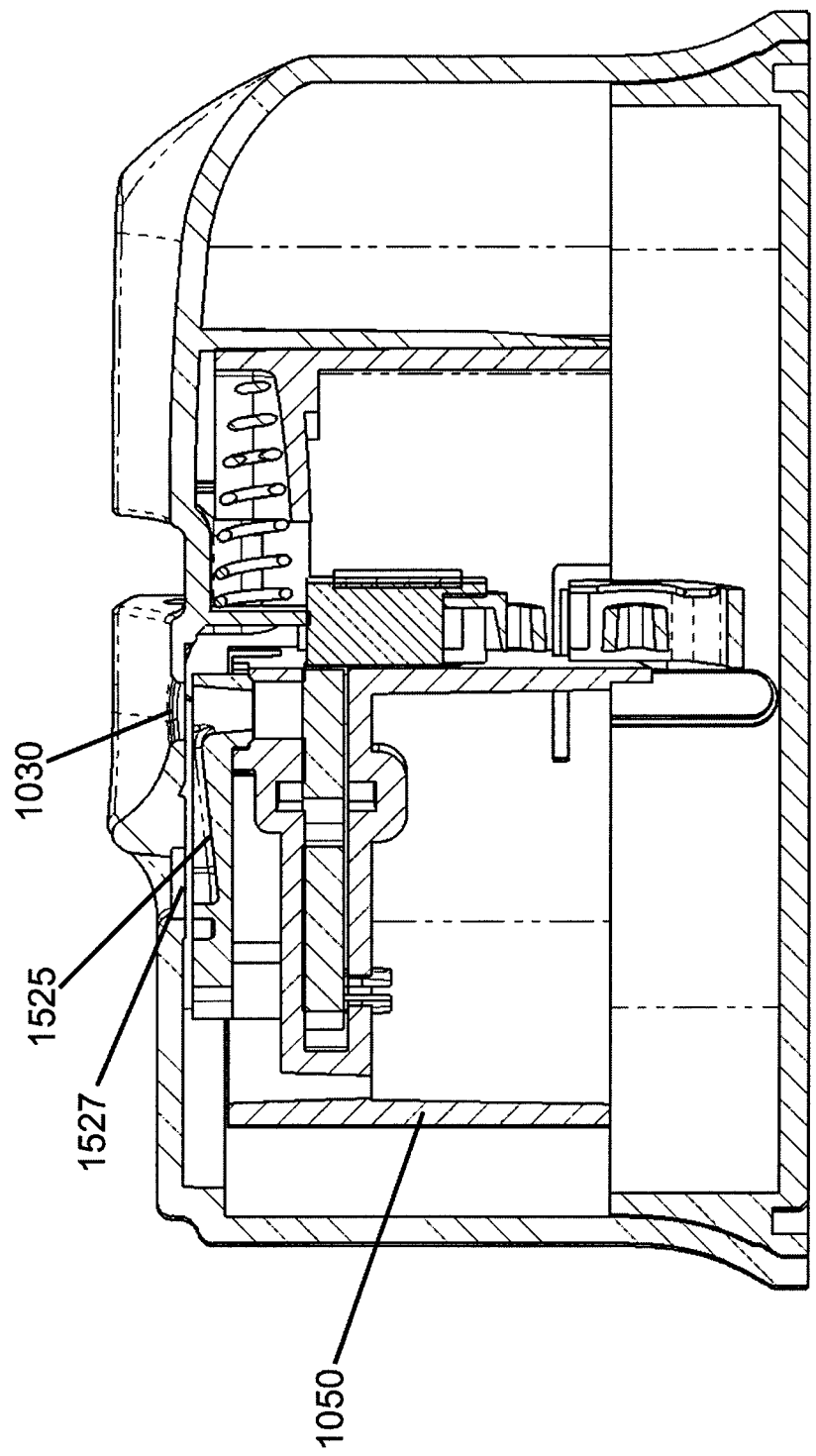
Figure 1H:
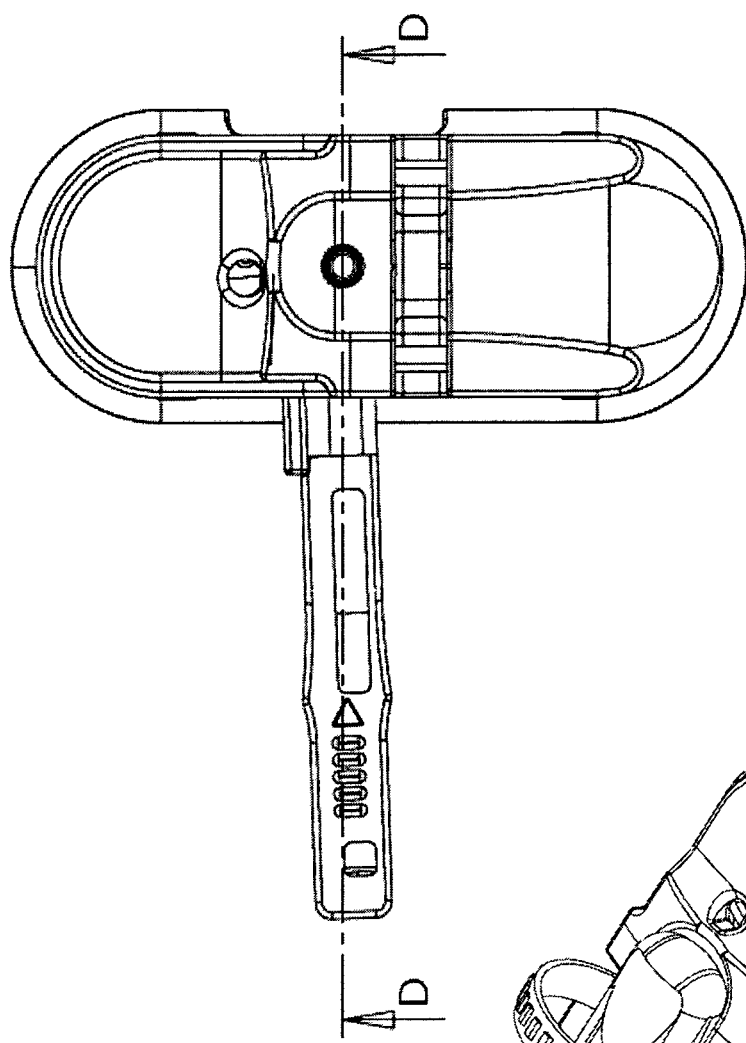
Figure 1I:
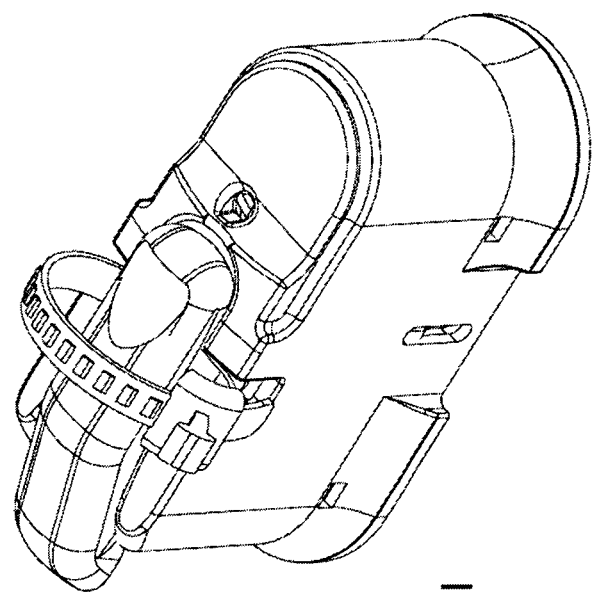
Figure 1J:
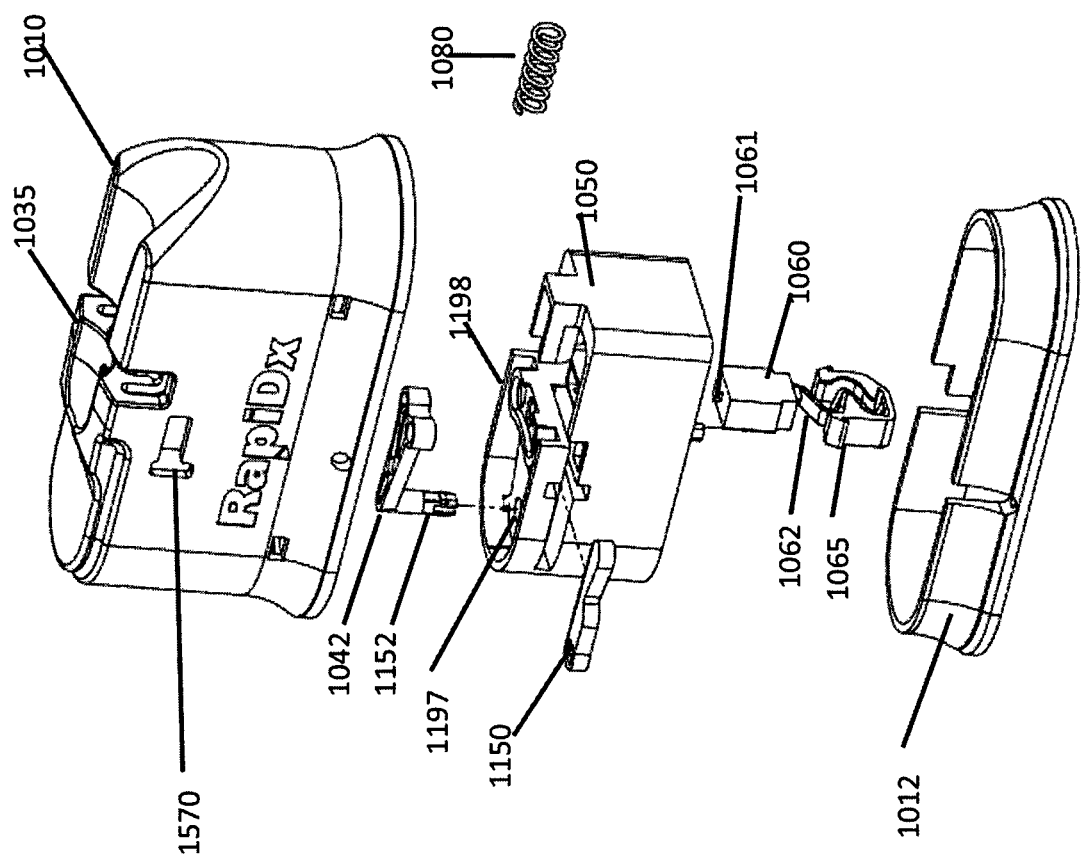

FIGS. 1A-1J schematically illustrate an example of an integrated device for blood piercing, sampling and testing according to the invention, wherein FIG. 1A is a cross-sectional view of the device illustrating the device in a sampling/testing position;

FIG. 1B is a similar cross-sectional view of the device illustrating the device in a piercing position;

FIG. 1C is a side cross-sectional view of the device while in its sampling position;

FIG. 1D is a side cross-sectional view of the device in a testing position thereof;

FIG. 1E shows another cross-sectional view of the device while in the sampling/testing position;

FIG. 1F is an isometric view of the device;

FIG. 1G is a top view of the device showing lines A-A, B-B, E-E along which the sectional views of FIGS. 1A, 1E and 1C respectively are taken;

FIG. 1H shows the similar top view of the device also showing line D-D along which the section view of FIG. 1D is taken, and a testing means;

FIG. 1I is an isometric view of the device showing a finger positioned on the finger support element; and FIG. 1J is an exploded view of the device.

Figure 2E:
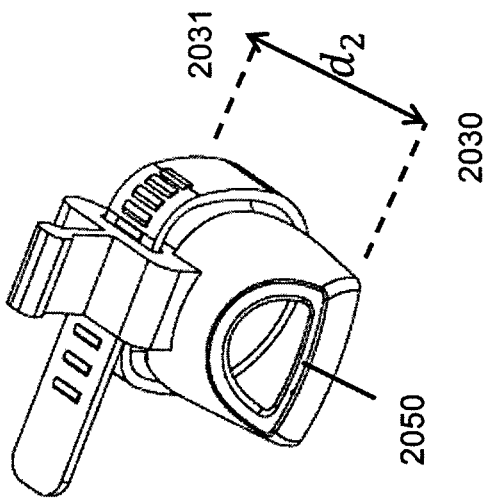
Figure 2F:
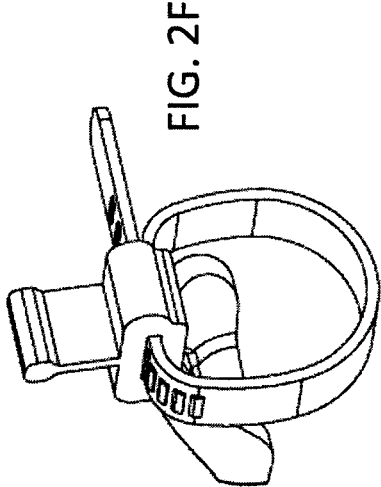
Figure 2H:
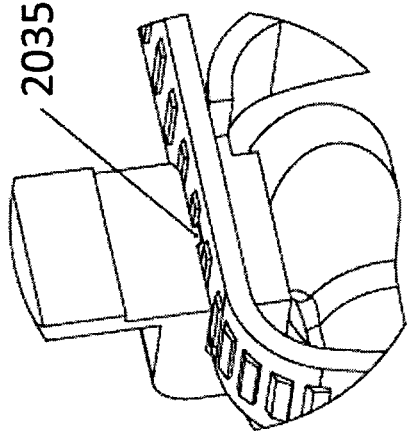
Figure 2G:
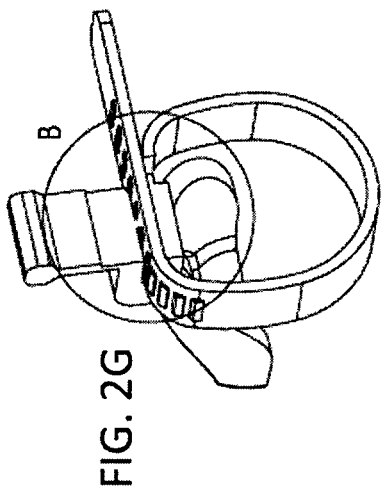

FIGS. 2A-2J exemplify a finger holder assembly of the present invention suitable to be used with the integrated device of the present invention, wherein FIGS. 2A-2D correspond to an opened position of the assembly (before fitting the finger), where FIG. 2A shows a front isometric view of the finger holder assembly; FIG. 2B illustrates more specifically the configuration of a cap-like part of said assembly, circle "B" showing the locking loop interior; FIG. 2C is a magnified isometric view of the locking loop; FIG. 2D shows a back isometric view of the finger holder assembly;

FIGS. 2E-2H correspond to a closed (ring-like) position of the finger holder assembly, where FIG. 2E is a front, magnified isometric view of the assembly; FIGS. 2G and 2F show a back isometric view of the assembly, where in FIG. 2G the locking loop element is shown in a sectional view to show more specifically the locking mechanism;

FIG. 2H is an enlarged view of the locking mechanism of FIG. 2G;

FIGS. 2I-2J show the finger holder assembly while being fitted on a user's finger.

DETAILED DESCRIPTION OF PREFERRED EMBODIMENTS

The present invention provides an integrated device including piercing, sampling and testing assemblies. This integrated configuration allows a user to extract and collect a blood sample from his finger and to immediately apply one or more required blood tests to the blood sample, while in comfort of his private settings without the need of any clinical assistance or a professional help. Moreover, the device of the invention permits a blood testing in a semi-automated or passive manner, i.e. permitting passive extraction of a blood sample, while the finger is maintained in substantially the same position with respect to the device during the sequential occurrence of piercing and sampling procedures and possibly also during the testing procedure, practically immediately one after the other.

Reference is made to FIGS. 1A-1J showing schematically a specific but not limiting example of the configuration and operation of an integrated device 1000 of the present invention. FIGS. 1A and 1B are cross-sectional views of the integrated device while in its sampling/testing position and piercing position respectively. FIGS. 1C and 1D are side cross-sectional views of the device while in its sampling and testing modes respectively, and FIG. 1E shows another cross-sectional view of the device while in the sampling/testing position. FIG. 1F and FIG. 1H, 1G show respectively an isometric view and top views of the device. FIG. 1I shows the device with a user's finger positioned on the finger support element; and FIG. 1J is an exploded view of the device. The invention will be described below with reference to all these figures.

The integrated device 1000 includes a housing 1070 which defines a finger site, generally at 1010, which may for example be in the form of a cavity (sampling cavity) and serves for supporting a user's finger or a portion thereof within said finger site during the device operation. The device includes piercing, sampling and testing assemblies, the configuration and operation of which will be described further below, and provides for sequential actuation of these assemblies to successively initiate piercing, sampling and testing operational modes of the device. Further provided in the device is a carriage 1050. The carriage is at least partially accommodated within the housing 1070 and is adapted for movement with respect to the finger site 1010 between a first position corresponding to the piercing mode of the device and a second position corresponding to the sampling and testing modes of the device.

The carriage incorporates or is connected to at least some of the elements of the piercing, sampling and testing assemblies, as will be described below. The carriage 1050 is movably mounted on a (horizontal) base 1012 which provides physical support to the device, especially needed during piercing and sampling. Preferably, such physical support includes, in this respect, the ability to maintain a steady and/or static location of the entire device and a position of the device on at least partially horizontal plane. In other words, an external bottom surface of the base 1012 is preferably provided with means for maintaining physical contact with a contacting surface. By way of non-limiting example, the surface can be that of a table which is typical in the private settings of the user. The base provides friction with the contact surface so as to resist the movement of the device during piercing and/or testing. Friction can be affected by application of rubber/plastic based layer adhesively coupled to the base 1012 thus preventing movement. Alternatively, a fabric layer or a sticker may be used to achieve similar function. The person skilled in the art would know to employ alternatives to affect such resistant or friction and prevent the movement of the integrated device during piercing, sample and testing.

Thus, in this example, the integrated device 1000 includes top housing 1070 defining finger site where the finger (or portion thereof) is to be located during the device operation. The finger site may be constituted by the finger support element 1010 (which is at least partially horizontal when the device is put in operation). The finger support element 1010 is, by way of non-limiting example, in the form of a finger recess or cavity which allows the user to position the finger (or portion thereof) during the device operation (in an at least partially horizontal angle).

The device 1000, at the finger site or the finger support element 1010, is formed with an orifice 1030 for allowing access (e.g. vertical passageway) for a piercing element 1061 (associated with the piercing means, and including blade or needle) to a finger under test. In this example, the orifice 1030 allows the piercing element to pass in an upright direction therethrough and perform the piecing procedure on the finger. The orifice 1030 enables the piercing element 1061 to reach and protrude the skin layer of the finger. The orifice is optionally positioned so as to ergonomically force or direct the user to position the finger exposing the optimal location for blood extraction at the middle of the top pad of the finger.

In addition, the orifice 1030 may be positioned at a certain predetermined distance from a location/site of the housing designed/intended for a finger holding assembly to enable application of pressure to the finger part. It should be noted that the housing is preferably formed with a projection/stopper 1020 defining the location of the finger tip surface when the finger is brought to the finger site. The piercing orifice is preferably made at a predetermined location (e.g. 10 mm) from said stopper. Optimizing the location of the piercing orifice (i.e. defining the piercing spot) with respect to the finger tip surface and the pressurized location on the finger, and preferably also optimizing the pressurizing location with respect to the finger tip, improves the device performance and the test results. As will be described more specifically further below, the finger holding assembly includes a pressure element, e.g. configured to apply pressure to a circumferential portion of the finger. As shown, in some embodiments, the location/site of the housing intended for the pressure element is formed as a depression/groove 1035 in the top housing.

The inventors have found that blood testing of clinical quality is dependent on the ability of a tester to extract a predetermined blood volume during the sampling (as described above), and also on the ability of the testing device to extract equal blood quantities in a repeated manner. This task can be facilitated by configuring the device so as to ergonomically force or direct the user to mutually position the finger and the finger holding assembly in an optimal mutual position which optimizes the blood flow upon piercing. The optimal location of the pressure element (of the finger holding assembly) on the finger is proximate to the distal interphalangeal joint of the pointing (or middle) finger or at about 6-13 mm measured from the middle of the top pad of the finger.

In some embodiments, the depression 1035 is located at a certain predetermined distance 1005 from the distal end 1020 of the finger support 1010, where this distance is selected so as to enable optimized application of pressure onto the finger when the pressure element of the finger holding assembly is located in the depression 1035. The optimal value (d) for the distance 1005 between the distal end 1020 and the depression 1035 is about 10-20 mm. On the one hand, this distance is selected to optimize and assure that a ring-like configuration of the finger holding assembly 2000 (or other clasping means) applies circumferential pressure at the optimal location on the tested finger. Additionally, it assures that the ring-like assembly 2000 or other clasping means provides circumferential pressure at the optimal distance from the piercing location defined by the position of the orifice 1030.

It should be understood that circumferential pressure or circumferential pressure element refers to a ring-like stretchable element capable of at least temporarily wrapping/hosting at least a circumferential portion of the finger of the user (preferably all the circumference) such that upon application of force (such as pulling or stretching a stretchable member) the application of tight pressure is effected upon the lateral circumference of the finger.

As indicated above, the integrated device 1000 comprises the movable carriage or assembly 1050. A motion path of the carriage with respect to the finger site defines at least two successive (horizontal) positions of the carriage corresponding to different operational modes of the device. These horizontal positions include a first, piercing position corresponding to a piercing mode of the device, and a second, sampling/testing position corresponding to a sampling/testing mode of the device. Thus, in some embodiments, movable carriage 1050 is mounted for reciprocating movement between the sampling/testing position (selection between sampling and testing can be provided by another structural features discussed below) and the piercing position.

It should be noted that the movement of the carriage 1050 can be permitted in the inner volume of the integrated device, i.e. hidden from the sight of the user. This further reduces the fear of pain typically suffered by such users.

Movement of the carriage can be implemented using a spring-like mechanism, constituted in this example by a spring ejector 1080, which is for example accommodated within a receiving cylinder 1081. The spring ejector 1080 is shiftable between its contracted and extracted states. Where the spring based ejector is contracted (as shown in FIG. 1A), the movable carriage 1050 can be positioned in the piercing position. The spring ejector 1080 being in the extracted/extended form can maintain the movable carriage in the sampling/testing position. Alternatively, the spring based ejector 1080 is extended in the piercing position, while being contracted to maintain the movable carriage in the sampling/testing position.

The use of a spring-like mechanism 1080 permits and operates the movable carriage 1050 to swiftly and/or immediately switch between the piercing and sampling/testing positions. The movable carriage 1050 facilitates or provides a carriage feed mechanism which will be elaborated herein below.

In the piercing position, a piercing element (such as a lancet) 1061 is horizontally aligned beneath the orifice 1030 (finger site). The piercing element 1061 is accommodated in a receiving element 1060, which is releasable attachable in a housing 1065 of the spring mechanism. Upon actuation (e.g. by user pressing a respective button), the spring like element 1062 accelerates the piercing element 1061 to protrude the orifice 1030 towards the finger placed in proximity to the orifice 1030 and to thus pierce the skin of the finger.

In some embodiments, the movable carriage 1050 being in the piercing position exposes the otherwise hidden piercing element 1061. On the other hand, in the sampling/testing position, the piercing element 1061 is in the contracted position and is thus hidden from the orifice line of sight.

In some embodiments, the piercing position facilitates horizontal alignment of the orifice 1030 with the piercing element 1061 while preventing alignment of the orifice with a blood holding element 1045.

In some embodiments, the sampling/testing position prevents alignment of the orifice with the piercing element 1061 while providing alignment of the orifice with the blood holding element 1045 (being an element of the blood sampling assembly).

The blood holding element 1045 is mounted on and carried by the carriage to be movable with respect to the finger site, i.e. to be brought to and away from the finger site. Optionally, a funnel assembly is provided, being for example mounted for (pivotal) movement with respect to the carriage (i.e., with respect to the blood holding element) and with respect to the finger site. The configuration and operation of the funnel assembly will be described further below. The blood holding element 1045 defines a blood collecting cavity (hollow liquid reservoir) enabling collection of blood in the liquid phase (rather than absorbing blood). The blood holding element is typically shaped like a cup or has some other cylindrically-like shape (e.g. hollow liquid reservoir) for collecting blood extracted from the finger by piercing. The element 1045 has a top opening 1048, side surfaces/walls 1046 and a bottom plate 1150. The bottom plate 1150 is shiftable between its closed position, in which it is aligned with the side surface thus closing the reservoir at the bottom thereof, and an opened position in which it is misaligned with the side walls thus forming a bottom opening 1047 of the reservoir. The opening 1047 is large enough to allow viscous fluid such as blood to pass therethrough by gravitation, optionally without active assistance, e.g. suction.

The blood holding element 1045 may thus be configured to be shiftable between at least two configurations: a closed configuration (when the bottom plate is aligned with the side walls), and an opened configuration (when the bottom plate moves away from the alignment position). In the closed configuration, the blood holding element 1045 accumulates fluid or blood therein. FIG. 1C illustrates the closed configuration, while FIG. 1D corresponds to the opened configuration. In the opened configuration, the blood holding element permits emptying or fluid evacuation. Preferably, emptying or fluid evacuation is actuated by gravitation. In the closed configuration, the bottom plate (stopper) 1150 contacts/is aligned with the side walls 1046 so as to prevent fluid passage through the bottom opening 1047 of the blood holding element 1045. To achieve fluid tight contact, the bottom stopper 1150 can be manufactured with a layer of elastomeric/rubber-like materials as a sealant. In the opened configuration, fluid impermeable bottom stopper 1150 is relocated to allow or permit fluid passage from the blood holding element 1045 downwards through the bottom opening 1047.

Shifting/displacing the blood holding element 1045 between the two configurations (opened and closed configurations) can for example be performed by directly manipulating the fluid impermeable bottom stopper 1150 to relocate and substantially evacuate the bottom opening. Alternatively, the blood holding element 1045 can be shifted between the two configurations by an external assistance or an externally applied force, such as by insertion of a test strip 1512 which applies mechanical force onto the bottom element 1150 in a horizontal direction to move it away from the reservoir, which is demonstrated in FIG. 1D. In some embodiments, the bottom stopper 1150 radially moves about an axis 1196 to swing between the opened configuration and the closed configuration.

As indicated above, the device may operate either in piercing and sampling modes, while a testing procedure is carried out by a separate testing device to which the blood sample in the blood holding element is brought, or operate in piercing, sampling and testing modes sequentially carried out within the device. If the use of an external test procedure is considered, then there is no need to shift the blood holding element from its normally closed position into the open position. This displacement is needed for the testing mode of the device itself.

Thus, the testing assembly may be constituted by the displaceable bottom plate of the blood holding element, and possibly also a slot made in the housing to be selectively used for inserting the test strip 1512 (or a portion thereof)

therein. Generally, the test strip is selectively insertable into a position in which a portion thereof is aligned with the reservoir (e.g. and also with a piercing orifice) to receive a blood sample from the reservoir (blood derived from the finger after piercing). The configuration may be such that the test strip is insertable into the slot made in the housing in a manner enabling sliding movement of the test strip towards and away from a location of alignment with the reservoir.

In particular, FIG. 1D illustrates the test strip 1512 being inserted into a slot made in the housing of the device, e.g. in the carriage. When the test strip is in such inserted position, it pushes the bottom stopper of the sampling assembly (of the reservoir) to move away from the finger site, and the test strip becomes vertically aligned with the test site. As a result, the fluid/blood is allowed to escape from the reservoir through the bottom opening 1047 by gravitation to thereby immediately interact with the test strip.

As indicated above, the device optionally includes a funnel assembly 1042. The funnel assembly 1042 is formed by a fluid/blood funnel part 1040 and optionally a reagent funnel part 1041. As demonstrated in the exploded isometric view of FIG. 1J, the funnel assembly 1042 is typically configured to define an axis 1152 which can be fitted/aligned in/with a vertical, cylindrically or tubular shaped, hollow groove having an opening 1197, the axis 1152 intersecting with said opening. The hollow groove permits displacement of the funnel element 1042 specifically from the blood sampling position and the testing position as detailed below. In the blood sampling position of the funnel assembly 1042, blood flowing from the pierced location of the finger is collected (i.e. sampled), while in the testing position of the funnel assembly, the testing procedure takes place.

In some embodiments, the blood funnel 1040 and the reagent funnel 1041 are mutually displaceable between different relative positions relative to the finger site such that in each position only one of the funnels can be aligned with the blood holding element 1045 (liquid reservoir). The mutual displacement may be actuated by manipulation of the funnel assembly 1042.

The blood funnel 1040 or funnel assembly 1042 can thus be actuated to be shiftable between at least two positions: blood sampling position and testing position. In some embodiments, the funnel assembly 1042 and the fluid impermeable bottom stopper 1150 are coupled together, optionally by mutual fixed engagement by axis 1152 or an axial coupling. If such coupling is utilized, the blood sampling position is simultaneously actuated together with the closed position of the blood holding element 1045. The testing position is simultaneously actuated together with the opened position of the blood holding element 1045.

In the blood sampling position, fluid funnel 1040 is aligned with the blood holding element 1045 and optionally further aligned with the orifice 1030. This alignment facilitates blood flow/drop/fall through the orifice 1030 into the blood holding element 1045 (e.g. hollow cup or reservoir), through the fluid funnel 1040. In the testing position, the reagent funnel 1041 is moved to be aligned with both the blood holding element and the test strip portion 1511.

It should be noted that typically prior to the alignment of the reagent funnel 1041 with the test strip portion 1511 the blood occupying the blood holding element 1045 has already been flowing from the reservoir and contacting the test strip at portion 1511. The shift to the testing position can provide clean reagent funnel 1041.

As indicated above, in some embodiments, the fluid funnel 1040 radially rotates about an axis 1196 to swing or shift between the blood sampling position and the testing position.

Generally, the provision of the fluid funnel is aimed at facilitating removal of excess blood from the reservoir (amount of blood above the predetermined volume defined by the volume of the reservoir), as well as facilitating indication of the full-reservoir state. The use of the fluid funnel actually corresponds to a two-part design of the liquid reservoir, as will be described below.

In some embodiments, the fluid funnel 1040 at its upper (top) portion 1520 is formed with a projecting slope 1525. During the blood sampling procedure, the fluid funnel 1040 is aligned with the blood holding element 1045, such that the fluid funnel forms an upper extension (top portion) of the reservoir 1045. When the reservoir 1045 together with its upper part 1040 becomes filled with the blood sample, i.e. the blood reaches the funnel end 1520, excess blood is cleared or removed from the blood holding element 1045 via the slope 1525 towards an indication window 1527. Excess blood removal is optionally provided by gravity. Where blood accumulates over the upper limit of the funnel end 1520 it slides/flows downwards along the slope 1525. To facilitate prompt clearance of blood through the slope, the latter may comprise a porous medium driving the excess blood to the proximity of the indication window 1527. The porous medium may be in the form of a capillary sponge layer over the slope 1525. A capillary tube or any other element may be used which "pulls" the blood into the indication spot.

In some embodiments, where blood accumulates over the upper limit of the funnel end 1520, prompt clearance of blood is provided by a porous medium driving the excess blood to the proximity of the indication window 1527 with or without the aid of a slope.

It should be understood that provision of the projecting sloped member for flowing the removed blood towards the indication window is optional, and if used it is not limited to the two-part design of the blood holding element (reservoir with removable funnel). Indeed, such a projecting sloped member may be formed at the top edge of the single-part reservoir. Thus, generally, if the provision of the projecting sloped member is considered, it may be associated with the removable top part of the two-part blood holding element or with the top portion of the single-part blood holding element (reservoir).

Also, as indicated above, collection of excess/residual blood (amount of blood above the predetermined volume defined by the volume of the reservoir), as well as indication of the full-reservoir state can be implemented using a collecting element such as capillary. This allows for identifying the full-reservoir state while collecting a less amount of excess blood.

The following is an example of the operational steps of the device 1000 of the present invention.

The device 1000 is placed on a horizontal plane such as a table. A user places his finger onto the finger support element 1010 to be at the finger site. Preferably, the finger is hold by the finger holding assembly, e.g. is inserted to a ring-like finger holding element 2000 (which will be described more specifically further below), which is fixedly located at the depression 1035. The finger holding element is tightened to ensure accumulation of blood in fleshy pouch of the finger or the middle of top pad in the finger extremity.

The device 1000 can be pre-set to a piercing position. Considering an optional use of the funnel element 1042, it may be brought to the blood sampling position at this initial piercing position of the device. Upon actuation of the piercing mode (e.g. pressing a button), the piercing assembly operates to release the piercing element (lancet) 1061 to move upwards to the finger at the finger site. The middle of top pad in the finger extremity is pierced by the lancet.

The movable carriage/device is then actuated (by the user or automatically) to shift to the sampling/testing position. Blood flows or falls by gravity (e.g. through the fluid funnel 1040) and accumulates within the blood holding element (liquid reservoir) 1045. At this stage, the blood holding element is in the closed position thereof which is required to collect fluid therein.

Blood is being collected (i.e. sampling mode proceeds) until the blood level reaches its maximum (e.g. reaches the funnel end 1525) and subsequently appears in the indication window 1527. Appearance of blood in the indication window 1527 indicates to the user that sufficient blood has been collected, corresponding to the end of the sampling mode. The user may thus release his finger by opening the apparatus 2000 or other clasp.

It should also be noted that the invention advantageously (from the physiological and environment point of views) provides for that the extracted blood is almost invisible during the whole procedure, while being present inside a closed system. This results in less cross blood contamination and much more hygienic procedures during the blood test.

The blood holding element 1045 can be actuated (automatically or by user manipulation) to be shifted into the opened position thereof, thereby actuating the testing mode. User can actuate the testing mode by inserting the test strip 1512 to a testing opening 1570, or by pushing the previously inserted test strip, to engage the bottom opening 1047 about the contact point 1151 and replace it by a portion of the test strip. Optionally, the funnel element 1042 is concurrently actuated to move to the testing position. The clean reagent funnel 1041 is thus placed vertically above the blood holding element 1045 (replacing the fluid funnel) so as to permit reagent passage therethrough. The opened position of the blood holding element 1045 permits deposit or evacuation of the collected blood sample (the desired amount thereof corresponding to the volume of the reservoir) onto the test strip. The fluid funnel structure having the funnel end 1520 limits the transfer of blood to the test strip to a predetermined maximal volumetric quantity. By way of non-limiting example, the predetermined maximal volumetric quantity is 2 drops or 25-75 microL. Certain maximal volumetric quantity can also be maintained by the fact the funnel element 1042 may shift horizontally if manipulated and thus physically remove the excess of blood that has been accumulated in the blood funnel volume 1040. There may be a reagent measuring element (not shown), which limits the transfer of the reagent to the test strip to be of a maximal volumetric quantity.

Thereafter, a test result appears in an appropriate results window on the test strip.

Reference is now made to FIGS. 2A-2H providing a schematic illustration of an example of the finger holding assembly 2000 according to the invention. The finger holding assembly 2000 is configured to apply pressure to a circumferential part of the finger, by using a circumferential pressure element. FIGS. 2A-2D demonstrate the finger holding assembly 2000 configured as a ring-like assembly in an open position thereof, and FIGS. 2E-2H demonstrate the ring-like assembly 2000 in its closed position for wrapping the finger portion. FIGS. 2I and 2J show the ring-like assembly 2000 while fitting the finger.

The finger holding assembly 2000 is used to actuate or facilitate circumferential pressure around a portion of the finger from which blood is drawn. In particular, the pressure is actuated on a specific finger portion which optimizes the blood withdrawal and substantially reduces pain involved in the finger piercing. The specific finger portion is at about the distal interphalangeal joint of the pointing finger (or middle finger) at about 6-13 mm measured from the middle of the top pad of the finger.

The finger holding assembly 2000 is therefore configured and operable to ergonomically force or direct the user to apply pressure to the specific position of the finger portion which optimizes the blood withdrawal and substantially reduces pain involved in the finger piercing.

The finger holding assembly 2000 includes a stretchable elastomeric elongated strip 2010 having a distal end 2011 and a proximal end 2012, and a loop member 2040 coupled to the elongated strip 2010 at the proximal end thereof. The loop member 2040 is typically manufactured from elastomeric material(s) such as rubber or rubber-like material, such as for example, silicone rubber.

The finger holding assembly 2000 thus includes a finger holding element 2010 configured to be fit on the finger such as to apply certain pressure to the finger. The finger holding element is a band or strip operable to be shifted from its open inoperative position to a closed-loop operative position in which it fits the finger. The band when in the operative position thereof applies certain pressure to the finger while preventing over-pressing of the finger, thereby reducing pain associated with the blood test.

The elongated strip 2010 is carried by or is provided with teeth or other projecting members 2015. The projecting members 2015 are configured to engage a locking tooth/member 2035 which is typically located in the interiors of the loop member 2045. The interior of the loop member 2045 is shown in a cross-sectional isometric view in FIG. 2C.

In some embodiments, the projecting members 2015 and the locking member 2035 are configured with appropriate geometry (shape and size) so as to be appropriately engaged. This engagement is such as to effect application of a circumferential pressure suitable for producing optimal blood flow through the pierced portion of the finger while restricting venous flow.

The inventors have found that the pressure range which optimizes the blood flow to the pierced portion of the finger also substantially reduces pain associated with the finger tip piercing. In particular, the inventors designed the projecting members 2015 and the locking member 2035 from silicone rubber (or other elastic material) in size(s) and dimension(s) to apply circumferential pressure of about 30-75 mBar. As explained further below, the material selection and design of the projecting members 2015 and the locking member 2035 permit retraction of the assembly at least in part in response to actuation of excessive force by the user.

This is based on the inventors' understanding that one the shortcomings of the conventional techniques of the kind specified is associated with that, according to this approach, a user has to releasably adjust a pressure element without knowing about the optimal pressure to be applied. Therefore, users (normally fear-full users) might apply excessive force on the finger which results in increased pain and also hinders the ability to perform the test adequately. Excessive pressure can also result in blood quantities which fall short of the minimum required for the blood testing.

Therefore, the finger holding assembly 2000 of the invention is configured and operable such that upon application of excessive pressure (or over-pressing) on the circumference of the finger, pressure is automatically relieved to the optimal pressure range. The projecting members 2015 and the locking member 2035 are configured to succumb or yield under the excessive force. In such a case, where excessive force is actuated by the user, the finger holding assembly 2000 is being retracted at least in part. The retraction continues until the circumferential pressure is reduced to the pressure level tolerated by the locking members 2015 being engaged with the projecting member 2035. Additional advantage in this respect is that pressure adjustment is provided without the subjective (sometimes erroneous) pressure perception of the user.

The finger holding assembly 2000 may also include a cap-like member 2020. The cap-like member 2020 is of a size and proportion to accommodate the finger of the user during piercing and sampling. The cap-like element 2020 is configured to accommodate at least a portion of the finger and has a distal end comprising a contact surface and a proximal end connected to a portion of the band 2010. The cap-like member is typically provided with a slit 2025 suitably positioned to permit the finger nail to protrude therethrough, and thus the finger conveniently abuts the distal end of the cap 2050.

Where the user fits his finger into the cap 2020, optionally permitting his finger nail to protrude from and through the slit 2025, he can circumferentially wrap the elongated strip 2010 around the finger. The distal end 2011 of the strip 2010 is inserted into the loop 2040 as schematically shown in FIG. 2E. The projecting member 2015 and the locking member 2035 are engaged and lock the elongated strip 2010 so as to produce the optimal or suitable circumferential pressure on a portion of the finger. If the user applies excess pressure, the projecting member 2015 and the locking member 2035 succumb or yield under the excessive force and are thus retracted at least in part to releasably produce the appropriate pressure range.

In addition, the cap-like member 2020 is preferably configured to optimize a distance between a pressure point (pressured location) 2031 and the distal end 2030 to a predetermined optimal value (d2) or range of values, for example 10-20 mm. Maintaining the optimal distance secures that pressure is actuated on a specific finger portion which optimizes the blood withdrawal and reduces pain involved in the finger piercing. The specific finger portion is at about the distal interphalangeal joint of the pointing (or middle) finger or at about 6-13 mm measured from the middle of the top pad of the pierced finger.

The finger holding assembly 2000 of the present invention can be used in conjunction or in combination with the above-described integrated device 1000 or any other device of the kind specified. Also, the use of the cap-like member 2020 in the ring-like finger holding assembly 2000 is optional. Typically, the finger holding assembly 2000 can be fitted or integrated in the depression 1035 which is suitably sized to accommodate its use.

Thus, the finger is brought in the operative position, and while the finger's position is kept, the device operates as follows: The device is brought into its piercing mode, and a piercing element is applied for piercing a finger portion (such as a finger tip); the device is shifted into a sampling mode, by manipulating one or more elements of the sampling assembly to a sampling position for collecting the blood sample in a blood holding element; and upon identifying that sufficient blood has been collected (i.e. equal to or above a minimum volumetric threshold), and further validating that excess blood (i.e. over a maximum threshold) is removed, the device is shifted into its testing position, while the user is allowed to remove his finger from its operative position.

Thus, through the entire orchestrated procedure, the finger can remain static in a finger cavity or another finger holding element (or generally located on a finger site), while the complex functionalities are actuated without assistance of clinical personnel.

It should also be noted that the integrated device of the present invention can be configured to carry out the piercing, sampling and testing procedures in a hands-free fashion for the user, i.e. the user does need not to support/hold the integrated device by hand. The user can position the integrated device on a table, for example, jus to provide a physical support required to maintain the device static during piercing, sampling and testing. Therefore, the individual using the device is relieved from the need to actively bring the piercing assembly to the proximity of the finger or finger tip, and thus may focus on merely placing the finger or finger tip at the appropriate cavity or support. This reduces the fear factor which is one of the major drawbacks of finger piercing assembly which typically require that user actively operates to bring the piercing assembly in the suitable position in proximity of the finger prior to piercing (which is deterring especially for unskilled users).

The integrated device of the present invention allows for using all the required reagents for blood testing, and due to the ability of the device to supply precise amount of blood for the blood test, allows blood testing in the private settings of the user while assuring that the test is of a quality comparable to that of the clinical settings. This is also facilitated by the control and protected environment created within the integrated device which allows the passive extraction as defined above. In particular, the structure of the device permits sequential, and immediately one after the other, execution of piercing, sampling and testing in a controlled manner which assures repeated piercing/sampling/testing conditions and thus increasing the confidence in the measurement performed. The integrated device can accurately and successively provide several operational states of the device namely: piercing, sampling and testing, starting one after the other in a predetermined order. It should be noted that generally the device may be configured such that the different procedures, while being successively started, occur in timely separated sessions or partially timely overlapping. By way of a non-limiting example, in a sampling state the testing cannot be performed and vice-versa. The inventors have found that under certain conditions simultaneous operations of sampling and testing inherently might reduce the accuracy of the measurement resulting from inaccuracies caused by user mistakes and variations resulting from fear induced by a blood drawing scenario.

As described above, the device preferably comprises a moving carriage which incorporates or is connected to at least some elements of the piercing assembly, the sampling assembly (a blood collecting/holding element) and the testing assembly. The carriage is displaceable with respect to a finger site, i.e. the finger location when in the operative position. Movement of the carriage in a certain direction (typically in a horizontal plane) relative to the finger site thus successively shifts the device through its piercing position, and sampling and testing position. The configuration may be such that a bottom plate of a liquid reservoir of blood holding element is additionally (e.g. linearly or pivotally) movable with respect to said carriage and said finger site between a closed position of the liquid reservoir (corresponding to the blood collection state) and an opened position of the reservoir (corresponding to the blood testing state). To this end, the device preferably utilizes a blood holding element in the form of a reservoir enabling collection and containing a liquid-phase blood sample. In other words, the reservoir is a container having a hollow cavity defining the blood volume required for the test. As described above, the use of such liquid container also facilitates indication of the sampling state to the user, i.e. whether the container has collected the sufficient blood amount or not, as well as whether there is no excess of blood during testing. As also described above, according to some embodiments, the device may comprise a reagent(s) holding unit, disposed vertically above a blood holding element, which, when in the testing position of the device, is aligned above the test strip.

As indicated above, the integrated device of the invention assures a precise blood volume collection, by defining both minimal volumetric quantity and maximal volumetric quantity for the accurate testing. Again, it ensures repeated and identical sampling/testing conditions which are the essence of providing blood testing with increased credibility. In addition, the blood test can also be performed on crude blood portion which can optionally be transported within the moving internal parts of the device without being flown through a porous media which may affect the testing results.

Table 1 exemplifies a relation between the different procedures (piercing, sampling and testing) with respect to the order of occurrence of these procedures and respective structural elements/assemblies with respect to one another, according to preferred embodiment of the invention.

closed to its opened position allowing the blood sample interaction with the testing means.

The device of the present invention is especially useful for diagnosing health conditions based on determination of concentrations, conductivity, viscosity, and the like of chemical and/or biological factors selected in a non-limiting manner from cholesterol, for assessing risk of heart disease; glucose, for monitoring diabetes; the presence of illegal drugs and drugs of abuse; hCG, to screen for pregnancy; HIV-antibody, for determining HIV infection; prothrombin time, for monitoring blood thinning and clotting; fecal occult blood, to screen for colorectal cancer; and luteinizing hormone, to predict ovulation or any combination thereof.

The device may according to some embodiments, require only a simple colorimetric chemical reaction for its operation, and may require no electricity or computer. However, in other modes of detection, such as fluorometric, electronic, or any other sensory-discernable signals are also within the scope of this invention. The device can be used anywhere, being lightweight, portable, and disposable. It provides rapid and accurate diagnosis based on exhaustively investigated biological, chemical or physical reactions with whole blood that have been perfected by the medical industry. Blood spillage is entirely avoided since the blood is conveyed immediately after it is drawn onto the test strip. Similarly, the entire volume of blood required is minimized, eliminating the health hazard of spillage and the psychological factors involved with the sight of blood, in addition to decreasing the physical pain associated with drawing a larger amount of blood.

TABLE 1

| Element/Assembly | Element conditions | | Device functionalities/states | | |
|---|---|---|---|---|---|
| | | | Piercing | Sampling | Testing |
| Movable carriage | Piercing(X) | Sampling/Testing(O) | X | O | O |
| Funnel assembly | Sampling(X) | Testing(O) | X | X | O |
| Blood holding element | Sampling(X)/closed | Testing(O)/opened | X | X | O |

As can be seen in the above Table 1, in the present example, the device of the present invention includes a movable carriage associated with (carrying or connected to) the elements of the piercing, sampling and testing assemblies; a funnel assembly optionally provided and being pivotally movable with respect to the carriage for selectively allowing the device operation in the sampling or testing mode; and a blood holding element shiftable between its closed position (sampling state) and opened position (testing state). The funnel assembly includes elements relating to the sampling and testing means, as will be described more specifically further below. The movable carriage is displaceable between its first position corresponding to the piercing mode of the device operation, and its second position corresponding to the sampling and testing modes of the device operation. When the carriage is in the first position (relative to the finger site), the device is operable in the piercing mode (denoted "x"), and when the carriage is brought to its second position, the device can successively perform the sampling and testing modes ("o"). While in the second position of the carriage, the position of the funnel assembly defines the device position corresponding to the sampling mode or the testing mode. In the same second position of the carriage, upon identifying that the required blood sample has been collected, a position of the funnel assembly shifts the blood holding element from its normally The device of the present invention may be used with a measurement device for non-invasively measuring one or more body parameters, e.g. blood glucose. The measurement device may be adapted to perform optical measurements and/or impedance-type measurements and/or photo-acoustic measurement and/or ultrasound tagging of light based measurements.

The references cited herein teach many principles that are applicable to the present invention. Therefore the full contents of these publications are incorporated by reference herein where appropriate for teachings of additional or alternative details, features and/or technical background.

It is to be understood that the invention is not limited in its application to the details set forth in the description contained herein or illustrated in the drawings. The invention is capable of other embodiments and of being practiced and carried out in various ways. Those skilled in the art will readily appreciate that various modifications and changes can be applied to the embodiments of the invention as hereinbefore described without departing from its scope, defined in and by the appended claims.

The invention claimed is:

1. A medical device for a blood test, the device comprising:
   (i) a housing defining a finger site for supporting a user's finger or a portion thereof within said finger site during the device operation;

(ii) piercing, sampling and testing assemblies sequentially actuatable to successively initiate piercing, sampling and testing operational modes of the device, the sampling assembly comprises a blood holding element configured as a two part element and comprising a first part being a hollow liquid reservoir for collecting and holding a predetermined volume of a liquid-phase blood sample freely flowing from the finger as a result of piercing, and a second part being selectively movable to be brought into an assembled position with said liquid reservoir thereabove, thereby forming a top portion of said blood holding element having a projecting sloped member and displaced into a dissembled position, thereby removing excess blood from said liquid reservoir, said hollow liquid reservoir comprises a bottom plate movable between a first position, in which it is aligned with side walls of said liquid reservoir, corresponding to a closed state of the reservoir keeping collected blood in said liquid reservoir, and a second position, in which it is misaligned with the side walls corresponding to an open state of said liquid reservoir allowing blood flow from said liquid reservoir for immediate testing procedure within the device;

(iii) a carriage at least partially accommodated within said housing and being adapted for movement with respect to said finger site between its first position corresponding to the piercing mode of the device and a second position corresponding to the sampling and testing modes of the device, the device being thereby capable of operating in the piercing, sampling and testing modes while at a static position of the user's finger.

2. A device according to claim 1, wherein the piercing assembly is accommodated inside said housing with respect to the finger site such that an operation of the piercing assembly in the piercing mode of the device is hidden from the user.

3. A device according to claim 1, comprising a finger holder element configured to be fit on the finger such as to apply pressure to the finger in a manner assisting in withdrawal of blood during the piercing and sampling modes and reducing pain associated with the blood test.

4. A device according to claim 3, wherein said finger holder comprises a band operable to be shifted from its open inoperative position to a closed-loop operative position in which it fits the finger, said band when in the operative position thereof applies the pressure to the finger while preventing over-pressing of the finger, thereby reducing pain involved in the blood test procedures.

5. A device according to claim 1, comprising a finger holder element configured to be fit on the finger such as to apply pressure to a certain location on the finger, said certain location being selected to be spaced a predetermined distance from at least one of the finger tip and a piercing orifice provided in said finger site.

6. A device according to claim 5, wherein said housing comprises a groove located within said finger site and being configured for immobilizingly receiving a portion of the finger holder element therein, thereby fixing a position of the finger with respect to said finger site, during the device operation, said groove being located at a predetermined distance from the piercing orifice, thereby ensuring the application of pressure to the finger by said finger holder element a certain predetermined distance from a location on the finger being pierced.

7. A device according to claim 1, wherein said housing comprises a protrusion defining a distal end of the finger site to be abutted by a finger tip during the device operation.

8. A device according to claim 1, wherein the piercing assembly comprises a piercing element movable along a first axis towards and away from the finger site and accessing the finger via an orifice in said finger site to perform piercing.

9. A device according to claim 8, wherein said piercing assembly is movable by said carriage along a second, intersecting axis, with respect to the finger site, between its first inoperative position in which the piercing element is not aligned with the orifice along the first axis and a second operative position in which the piercing elements is aligned with said orifice along the first axis.

10. A device according to claim 1, wherein the blood holding element is configured such that, when in the sampling mode of the device, the blood holding element has a top portion formed with a projecting sloped member for flowing a portion of collected blood volume above said predetermined volume out of a liquid reservoir towards an indication window, appearance of blood in the indication window being indicative of the blood holding element contains the predetermined volume of blood.

11. A device according to claim 1, wherein the testing assembly comprises a slot made in said housing for a test strip to be at least partially inserted therein in a manner enabling sliding movement of a test strip towards and away from a location of alignment with the piercing orifice.

12. A device according to claim 1, wherein the testing assembly comprises a test strip insertable into a position in which a portion thereof is aligned with a piercing orifice to receive a blood sample from the finger after piercing.

13. A device according to claim 1, wherein said carriage incorporates or is connected to elements of the piercing, sampling and testing assemblies such that the movement of the carriage with respect to the finger site successively brings said elements into an operative position in which the element of the respective assembly is aligned with the finger site corresponding to said first and second positions of the carriage.

14. A device according to claim 1, comprising a reagent holding unit mounted to be selectively brought into alignment position with respect to an element of the testing assembly, when in the testing mode of the device.

15. A system comprising:
(i) the blood test device according to claim 1; and
(ii) a measurement device for non-invasively measuring one or more body parameters.

16. A system according to claim 15, wherein the measurement device is configured and operable for non-invasive measurement of a blood glucose.

17. A system according to claim 15, wherein the measurement device comprises a ring-shaped sensor.

18. A system according to claim 17, wherein the ring-shaped sensor is adapted to be placed on the finger in addition to a finger holding element for use in the blood test.

19. A system according to claim 15, wherein the measurement device comprises a finger encompassing element for applying pressure to the finger.

* * * * *